(12) United States Patent
Jensen et al.

(10) Patent No.: US 10,638,959 B2
(45) Date of Patent: May 5, 2020

(54) ORAL PH AND BUFFERING CAPACITY MODIFIERS

(71) Applicants: Steven D Jensen, South Jordan, UT (US); Densen Cao, Sandy, UT (US)

(72) Inventors: Steven D Jensen, South Jordan, UT (US); Densen Cao, Sandy, UT (US)

(73) Assignee: CAO Group, LLC, South Jordan, UT (US)

( * ) Notice: Subject to any disclaimer, the term of this patent is extended or adjusted under 35 U.S.C. 154(b) by 0 days.

(21) Appl. No.: 15/708,314

(22) Filed: Sep. 19, 2017

(65) Prior Publication Data

US 2018/0000392 A1 Jan. 4, 2018

Related U.S. Application Data

(62) Division of application No. 13/072,490, filed on Mar. 25, 2011, now abandoned.

(60) Provisional application No. 61/317,602, filed on Mar. 25, 2010.

(51) Int. Cl.

| | |
|---|---|
| *A61B 5/145* | (2006.01) |
| *A23G 3/36* | (2006.01) |
| *A23G 3/50* | (2006.01) |
| *A23G 4/06* | (2006.01) |
| *A23G 4/18* | (2006.01) |
| *A61K 8/67* | (2006.01) |
| *A61K 31/375* | (2006.01) |
| *A61K 33/00* | (2006.01) |
| *A61K 33/16* | (2006.01) |
| *A61Q 11/00* | (2006.01) |
| *A61B 10/00* | (2006.01) |

(52) U.S. Cl.
CPC ............ *A61B 5/14539* (2013.01); *A23G 3/36* (2013.01); *A23G 3/50* (2013.01); *A23G 4/06* (2013.01); *A23G 4/18* (2013.01); *A61B 5/14507* (2013.01); *A61K 8/676* (2013.01); *A61K 31/375* (2013.01); *A61K 33/00* (2013.01); *A61K 33/16* (2013.01); *A61Q 11/00* (2013.01); *A61B 10/0051* (2013.01); *A61K 2800/52* (2013.01)

(58) Field of Classification Search
CPC ..................................................... G01N 33/554
USPC ...................................... 435/7.32; 433/217.1
See application file for complete search history.

(56) References Cited

U.S. PATENT DOCUMENTS 3,525,791 A * 8/1970 Ahrens ................ A61K 8/0216
514/474

OTHER PUBLICATIONS

GC, "saliva testing: Good Practice Good Sense." www.gcaustralasia. corn/Upload/pdf/976/Brochure-Saliva-Check-BUFFER.pdf. published online Jul. 10, 2008 (Year: 2008).*

* cited by examiner

*Primary Examiner* — Walter E Webb

(57) ABSTRACT

Example embodiments of the present invention include various compositions that include a pH modifier composition and/or a buffering capacity modifier composition. In some examples, the pH modifier compositions include a dose of pH modifier to raise the pH in a patient's mouth from about 1 to about 2 pH levels. The compositions are then incorporated into various confections for oral ingestion or application that allow a patient to easily use the composition with the pH and/or buffering capacity modifiers. For example, compositions with the pH and/or buffering capacity modifiers can be incorporated within chewing gum, tablets, lozenges, breath strips, hard candy, oral sprays, and other confections. Another embodiment of the invention includes a testing device to test the pH and buffering capacity within a patient's mouth.

10 Claims, No Drawings

ORAL PH AND BUFFERING CAPACITY MODIFIERS

CROSS-REFERENCE TO RELATED APPLICATIONS

This application claims the benefit of U.S. application Ser. No. 13/072,490 filed Mar. 25, 2011, which claims priority to U.S. Provisional Application No. 61/317,602, filed Mar. 25, 2010, and U.S. Provisional Application No. 61/353,609, filed on Jun. 10, 2010. The content of each of the aforementioned applications is incorporated herein by reference in its entirety.

TECHNICAL FIELD OF THE INVENTION

The present invention relates to the field of cavity prevention by controlling the environmental factors found within the oral cavity that may cause tooth decay.

BACKGROUND OF THE INVENTION

Most people will at one point or another experience tooth decay that eventually leads to a cavity. To the average person, cavities are small annoyances that a dental professional can easily correct by removing the cavity and replacing the decay with some type of dental filling. Some individuals, however, experience tooth decay more than others. In particular, a portion of the population deals with rampant cavities that are difficult to contain and control.

Recent advances in dental science have helped dental professionals to more fully understand the causes of tooth decay and cavities. Many studies suggest that a person's diet may drastically affect the chances of getting a cavity. In particular, many experts argue that diets high in carbohydrates and other sugars, and lower in meat and whole grains, cause an increased risk of cavities. For example, studies have suggested that diets high in carbohydrates may cause oral micro-flora to become imbalanced, which may lead to increases risk of tooth decay, and ultimately an increased risk of cavities.

Modern microorganism studies have confirmed that the main bacterial culprits of tooth decay do indeed feed on carbohydrates, and other sugars that make up the building blocks of carbohydrates. Studies have also shown that of all the bacterial culprits responsible for tooth decay, the bacterium known as Streptococcus mutans is the bacterium with the most influence on causing tooth decay.

Streptococcus mutans depends entirely upon human hosts for its survival and progresses through a standard cycle of events with its host. The cycle begins with inoculation of an infant soon after birth by parental contact. Streptococcus mutans can be transmitted through saliva and is highly contagious. In order for Streptococcus mutans to become a permanent resident in the oral environment, the bacterium must attach somewhere in the oral cavity. By attaching to a site within the oral cavity, the Streptococcus mutans may colonize and avoid being washed to the stomach by saliva. Unfortunately, the human oral environment provides ample attachment sites for Streptococcus mutans as there are various crevasses to inhabit such as the gingival margin, spaces between teeth, etc.

After the Streptococcus mutans finds an attachment site, the process of tooth decay begins. The process begins when Streptococcus mutans consume sugar and excrete lactic acid as a waste product. As is well known, tooth enamel is composed entirely of mineral rods of calcium hydroxyapatite, which is susceptible to dissolution in acidic environments. The residual food that remains lodged in the oral cavity after eating provides the nutrient source for Streptococcus mutans to digest, which therefore produces the lactic acid that eventually dissolves holes in the enamel.

Once the lactic acid has produced holes in the teeth the decay process intensifies because the holes create even more protected space for food and the Streptococcus mutans to occupy. The rate at which the Streptococcus mutans digests carbohydrates and produce lactic acid can exponentially increase, causing tooth decay to exponentially increase, which can lead to a cavity in a fairly short amount of time.

Providing quality oral hygiene in the fight against cavities requires a direct understanding and plan to deal with the lactic acid produced from the Streptococcus mutans. The most common prevention method today is brushing the teeth with a fluoride dentifrice (tooth paste). First, the toothbrush allows a person to remove the excess food after he or she eats, and thereby deprive the Streptococcus mutans of an available nutrient source. Second, the toothbrush stirs up or aggravates the bacteria and dislodges it from attachment sites, thereby impeding colony progression and growth.

As far as the toothpaste's function, the toothpaste's primary function is to deliver a dose of fluoride to tooth enamel. Fluoride may chemically change the calcium hydroxyapatite of tooth enamel into a more acid resistant composition of calcium fluoroapatite. The process of fluoroapatite synthesis takes advantage of the electronegative reactivity of the fluoride ion during the natural re-mineralization cycles between the tooth and saliva, causing the tooth enamel to be more resistant to acid environments.

Although brushing the teeth helps fight tooth decay, toothbrushes and toothpaste are purely preventative measures and do nothing to address the eradication of the Streptococcus mutans. The eradication of the offending microorganisms was at one time thought to be the ultimate end of restorative dentistry. Research eventually produced the antibiotic "tetracycline" that was intended to wipe out tooth decay from the human race once and for all. This project ended in abysmal failure; instead, tetracycline treatment resulted in tetracycline resistant Streptococcus mutans, with the children of these patients being stricken with brown to green mottled teeth. It is now generally understood that microorganisms are very adaptable and usually evolve faster than antibiotics can be produced.

The foregoing leaves the toothbrush and fluoride as the essential means to combat tooth decay. The toothbrush and toothpaste, however, have disadvantages that decrease their effectiveness in the overall prevention of tooth decay. The biggest disadvantage is patient compliance. For example, most people brush twice a day and it is usually before breakfast and after dinner. The most effective time to brush is after eating to immediately remove any food left behind in the oral cavity. Moreover, the average person brushes less than 60 seconds at a time. In order for the fluoride in the toothpaste to have any positive effect, a person must brush for at least 60 seconds or longer.

There are several reasons that most people to not brush properly. For example, brushing teeth is not always convenient. To brush after every meal a person would have to deal with the annoyance of carrying a toothbrush and toothpaste during the day. Additionally, the person would have to find a convenient place to brush his or her teeth, which is another annoyance. Finally, after brushing a patient has to deal with a wet toothbrush and where to store it. In contemporary lifestyles the toothbrush and toothpaste are consigned for home use because that is the time and location when a person can most easily and conveniently brush their teeth and store the toothbrush and toothpaste.

As indicated above, the time when most people brush their teeth is the least effective time to brush teeth. In particular, the largest variances in oral pH happen after each meal corresponding with the cycle of sugar consumption by the Streptococcus mutans into lactic acid. In the early 20th century many studies were completed measuring the oral pH of patients as it relates to time and events. The general conclusions from these studies give us a better understanding of the oral environment. The general conclusions are as follows:

a. The average pH of oral saliva varies between individuals, yet the average pH of an individual stays fairly constant. The pH of some individuals within a group may differ in range from as wide as 5 to 8, yet the pH of each individual within the group would remain fairly repetitive. This conclusion may explain why some people have such a large problem with getting cavities, while others do not.
  b. The largest drop in pH of saliva happens after eating, followed by a slow rise in pH. The average pH drop of oral saliva after eating is between about 0.5-1.0 in healthy patients. The change in pH spikes at about 15-20 minutes after eating, followed by a gradual rise back to normal levels in about 60 minutes.

Among other conclusions, these studies indicated that the pH level of saliva was a major factor in tooth decay of an individual. The more acidic the saliva, the greater risk of tooth decay.

In addition, studies have also shown that it is not the pH levels of the saliva alone that cause cavities. An additional factor that can affect the rate at which dental caries occur concerns the buffering capacity of the salvia. Buffering capacity relates to the ability of a buffer—e.g., a partially neutralized acid—to resist changes in pH. Salts such as sodium citrate or sodium lactate are common buffers used to partially neutralize an acid. In patients that tend not to easily get cavities, their saliva is usually shown to have an increased buffering capacity.

In sum, clinical studies have shown that the greatest correlating cause of tooth decay between patients is the pH and the buffering capacity of their saliva. In order to adequately address prevention of tooth decay, both the pH and buffering capacity of saliva must be controlled. Some conventional products have been developed to attempt to address the pH issue of saliva. For example, conventional products that contain ingredients such as sorbitol, xylitol and other sugar free sweeteners claim to be helpful in restoring pH levels after a meal. These conventional products, however, do not chemically modify the saliva, but rather simply increase and stimulate natural saliva flows after a meal. Although increasing the saliva flow is more beneficial than doing nothing, the rate at which the pH level within the saliva is normalized is slow, which may still allow tooth decay.

What is needed is a dental treatment which quickly and efficiently adjusts pH levels within the oral cavity, increases the buffering capacity of salvia, avoids side effects, and provides a product suitable for simple patient compliance.

SUMMARY OF THE INVENTION

Example embodiments of the present invention include various compositions that include a pH modifier composition and/or a buffering capacity modifier composition. In some examples, the pH modifier compositions include a dose of pH modifier to raise the pH in a patient's mouth from about 1 to about 2 pH levels. The compositions are then incorporated into various confections for oral ingestion or application that allow a patient to easily use the composition with the pH and/or buffering capacity modifiers. For example, compositions with the pH and/or buffering capacity modifiers can be incorporated within chewing gum, tablets, lozenges, breath strips, hard candy, oral sprays, and other confections. Another embodiment of the invention includes a testing device to test the pH and buffering capacity within a patient's mouth.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

DETAILED DESCRIPTION OF THE INVENTION

Example embodiments of the present invention include various compositions that include a pH modifier composition and/or a buffering capacity modifier composition. In some examples, the pH modifier compositions include a dose of pH modifier to raise the pH in a patient's mouth from about 1 to about 2 pH levels. The compositions are then incorporated into various confections for oral ingestion or application that allow a patient to easily use the composition with the pH and/or buffering capacity modifiers. For example, compositions with the pH and/or buffering capacity modifiers can be incorporated within chewing gum, tablets, lozenges, breath strips, hard candy, oral sprays, and other confections. Another embodiment of the invention includes a testing device to test the pH and buffering capacity within a patient's mouth.

By using example embodiments of the present invention, patients will have a convenient product to use to fight tooth decay and cavities. For example, patients can use the composition right after a meal during the time that the pH level in the mouth is most acidic. Moreover, embodiments of the present invention allow patients to fight tooth decay without having the annoyance of carrying a tooth brush or tooth paste with them wherever they go.

Furthermore, example embodiments of the present invention provide patients with a more effective way to fight cavities than regular gum or candy that simply promote saliva flow. In particular, example embodiments of the present invention actually chemically change the pH levels and/or buffering capacity of saliva such that the pH levels in the oral cavity are returned to a pH balanced or less acid state quickly and efficiently. Notwithstanding the various improvements to the fight against tooth decay, example embodiments of the present invention generally provide devices and methods to increase the buffering capacity of saliva and raise the pH within the oral cavity to a less acidic state.

Example embodiments of the present invention can include a buffering capacity modifier composition that includes any soluble or insoluble compound found in saliva that increases the buffering capacity of saliva. Example buffering capacity modifier compositions that increase the buffering capacity of saliva are the soluble and insoluble salts of calcium. Examples of salts that are useful in buffering capacity modifier compositions are calcium phosphate tribasic, calcium phosphate di-basic, calcium phosphate monobasic, calcium lactate, calcium citrate, calcium ascorbate, calcium carbonate, calcium hydrogen carbonate, calcium hydroxide, protein bound calcium and any other useful saliva buffering compounds.

The most preferred buffering capacity modifier compositions are those salts that are water soluble at pH above about 6. The solubility of the calcium salt in water allows the calcium ion to become available for natural re-mineralization processes that occur between the saliva and tooth on a readily basis. Some salts are more soluble in water than others, as illustrated in the table below. Salts with a high solubility in water such as calcium lactate and calcium ascorbate are especially useful. Mono-calcium phosphate is also effectively soluble in water.

| Calcium Salt | Solubility in water g/100 ml |
| --- | --- |
| Calcium lactate pentahydrate | 9 grams |
| Calcium ascorbate (citrate) | 43.6 grams |
| Calcium stearate | Insoluble |
| Calcium carbonate | 0.001 grams |
| Tri-calcium phosphate | Insoluble |
| Di-calcium phosphate | 0.02 grams |
| Calcium hydroxide | 0.173 grams |
| Mono-calcium phosphate | 22 grams |

We analyzed the immediate release of calcium ion of various salts by a calcium test kit by EM Quant and found that the most readily available calcium ion source is calcium ascorbate and calcium lactate. In particular, calcium ascorbate provided calcium ions on contact with water, and is therefore a good candidate for the buffering capacity modifier composition.

A combination of salts can be utilized to maximize the effects of the buffering capacity with respect to re-mineralization and pH. A preferred delivery device of the present invention comprises both pH modifier compositions and buffering capacity modifier compositions. Therefore, the delivery device can be designed to increase both the pH and the buffering capacity of saliva that neutralizes acids, raises the pH level above about 7, and floods the saliva with acid buffering salts. The same buffering salts also can act as a re-mineralization agent.

In addition, example embodiments of the present invention include the use of these same pH modifier compositions incorporated into a fluoride dentifrice in order to combine the synergistic effects of both a higher pH environment coupled with the beneficial qualities of the fluoride ion. For example, the fluoride ion may be incorporated into any of the pH modifier compositions of the present invention, especially in lower doses, such as below 100 ppm. The objective being to raise the pH of oral saliva along with the steady release of fluoride ion over longer periods of time versus the dose received through conventional tooth brushing. It is also within the scope of this invention to incorporate an abrasive, such as fine silica or diatomaceous earth into the confection that would aid in the physical removal of oral debris while chewing.

As summarized above, the preferred pH modifier composition of the present invention includes a pH modifier that raises the pH of oral saliva of the average person in a range from about 1 to about 2 to temporarily raise the pH of oral saliva firmly and safely out of the acidic range following eating. The elevated pH level counteracts acids produced by Streptococcus mutans and other organisms acting on food particles in the mouth remaining after eating.

Example pH modifier compositions can comprise those basic compounds that are safe for human consumption, and at the same time, can be used in the smallest quantities to deliver the biggest change in pH. For example, the pH modifier compositions of example embodiments of the present invention can raise the pH level of oral saliva with a minimum quantity of pH modifier composition such that the only parts of the body receiving a significant impact are isolated within the oral cavity. Insignificant quantities of the pH modifier composition swallowed during digestion would have a negligible effect on the stomach, as such are neutralized quickly by stomach acid.

Examples of the pH modifier compositions of the present invention include, but are not limited to, alkali salts and oxides such as the hydroxides, oxides and carbonates of magnesium, sodium, potassium, and calcium. Also included are any soluble salts of transition metals that can be made by various methods alkaline in an aqueous environment such as iron hydroxide and zinc hydroxide. Even further examples include amines and alkyl amines such as ammonia, diethylamine, dimethyl amine, hydroxylamine, quinoline, triethanol amine, triethylamine, ethylamine and methylamine and others. Additional pH modifier compositions include the alkaline salts having moderate to strong bases such as sodium carbonate, sodium hydroxide, potassium hydroxide and potassium carbonate.

The pH modifier(s) compositions can be dosed depending on the size, weight, solubility rate, and chosen basic compound into the confection of choice. The final dosage is that concentration necessary to provide an average change in oral pH by at least about 1 to about 2 pH. In other example embodiments, however, compounds producing pH modification ranges higher than about 1 to about 2 pH for those patients that have extremely acidic oral cavity properties. In short, the objective of example pH modifier compositions is to bring the oral pH following a meal to levels slightly higher than normal, but other pH modification ranges are also within the scope of this invention.

One example embodiment of the present invention includes a delivery device in the form of chewing gum that contains a pH modifier composition and/or a buffering capacity modifier composition. Chewing gum offers an ideal substance that is chewed but not swallowed providing a convenient way to deliver the pH modifier, buffering capacity modifier and/or fluoride at a steady rate. Other example confections can include, but are not limited to, lozenges and hard candies that are sugar-free.

Notwithstanding the type of delivery device used, the effect is to deliver pH modifiers and buffering capacity modifiers in a manner that releases the pH modifier and buffering capacity modifiers at a near constant rate. A chewing gum is ideal for this delivery because it is not swallowed like a lozenge or a hard candy, as these may be crushed with the teeth and broken down prematurely into pieces and swallowed. The downside to chewing gum is that the release rate of the pH modifier and/or buffering capacity modifier is greatest at the beginning of chewing and decreases in time. Conversely, the lozenge or hard candy, if not crushed into pieces, can provide a more constant release rate of the pH modifier and/or the buffering capacity modifier.

The delivery device confections can be made with carbohydrate substitutes as the bulk material that makes the body of the candy. These sugarless confections accelerate the natural neutralization cycle of the oral cavity by stimulating saliva flow, while delivering the pH modifier. As can be understood, any similar item that can be chewed or dissolved within the mouth following a meal would be effective as long as the item did not contain cariogenic sugars and/or carbohydrates. When added as bulk material, the functions of these non-cariogenic sweeteners like xylitol, sorbitol, phenylalanine, sucralose, saccharin and others are to make the delivery devices or confections sweet, and therefore more palatable.

The delivery devices and compositions of the present invention can raise the pH level and buffering capacity of oral saliva rapidly since oral acid is neutralized into a salt by an acid base reaction with a known basic compound. This actual change in the pH level and buffering capacity of the oral saliva is unique compared to conventional compositions that don't chemically change the saliva, but rather depend on the dilution and rinsing effects of saliva.

Many other confections containing pH modifiers are also within the scope of this invention, as long as they meet the general objective to combine a pH modifier composition and/or a buffering capacity modifier composition with a traditional confection that can be conveniently and inconspicuously administered following a meal. Another example embodiment is a breath strip. In particular, the breath strip can be a thin water-soluble composition that is intended to dissolve in the mouth. As the breath strip dissolves, the pH modifier and/or the buffering capacity modifier can be released from the breath strip, thus adjusting the pH levels and buffering capacity within the mouth and saliva.

In another example embodiment, the delivery device can be in the form of an oral spray or rinse. For example, the pH modifier composition and/or the buffering capacity composition can be dissolved into a liquid spray or rinse that a patient can spray or rinse in their mouth. Because the spray or rinse will likely not provide a long lasting release of the pH modifier and/or the buffering capacity modifier, the dosage of the pH modifier and/or buffering capacity modifier can be greatly increased to provide a quick and efficient way to raise the pH level within the oral cavity and saliva.

Various colors, scents, flavors and other ingredients can be used with all the example embodiments to increase flavor, visual athletics, and overall presentation of the various delivery devices and compositions.

The following examples illustrate various example embodiments of delivery devices used to deliver the pH modifier composition and/or the buffering capacity modifier composition. The following formulations are for example purposes only, and illustrate only specific compositions and delivery devices according to the broader principles described above.

Example 1

In one example embodiment of the invention, a chewing gum including a pH modifier composition and a buffering capacity modifier composition comprises the following components within the percentage weight ranges in the following table.

| Example 1 | |
|---|---|
| Component | % Wt Range |
| Gum Base | 32-42% |
| Xylitol | 35-45% |
| Sorbitol | 11-21% |
| Sucralose | 0.1-1% |
| Flavoring | 0.1-1% |
| Coloring | 0.01-0.1% |
| Calcium Ascorbate | 1%-10% |
| Sodium Carbonate | 0.01%-0.05% |

For example, and according to the general ranges of percentage weight described above, one particular example embodiment of a chewing gum containing pH and buffering capacity modifier compositions comprises: a gum base (37.94%); xylitol (40.00%); sorbitol (16.00%); sucralose (0.20%); peppermint oil (0.40%); methyl salicylate (0.40%); glycerin (1.00%); brilliant blue lake color (0.05%); calcium ascorbate (4.00%) and sodium carbonate (0.01%). The resulting composition is blended in a sigma blade mixer until homogenous, followed by forming the homogeneous mixture into a shaped gum using a mold compression method. The resulting compressed gum is ready to chew.

Example 2

In one example embodiment of the present invention, a hard candy formulation comprises the following components within the weight percentage ranges in the following table.

| Example 2 | |
|---|---|
| Component | % Wt Range |
| Xylitol/Sorbitol | 80-97% |
| Calcium Ascorbate | 1%-10% |
| Sodium Carbonate | 0.01%-0.05% |
| Methyl salicylate | 0.1-1% |
| Flavoring | 0.1-1% |
| Coloring | 0.01-0.1% |

For example, and according to the general ranges of percentage weight described above with respect to Example 2, one particular example embodiment of a hard candy containing a pH and buffering capacity modifier compositions comprises: xylitol or sorbitol (95.19%); calcium ascorbate (4.00%); sodium carbonate (0.01%); peppermint oil (0.40%); and methyl salicylate (0.40%). The sugars are melted and mixed until the composition reaches a hard candy stage, followed by addition of the other ingredients. The resulting mass is allowed to cool and is then cut into single serving-sized pieces while still in a moldable state, after which the sized pieces are allowed to further cool into hard candy.

Example 3

A third embodiment of the present invention comprises a liquid rinse or oral spray. Since an aqueous solution of sodium carbonate and soluble calcium salt will eventually react to produce nearly insoluble calcium carbonate, it is preferred to deliver a 2-part composition in a dual chambered spray device, or alternatively use a pH modifier that will not react with calcium ion, for example, sodium hydroxide. An example of a 2-part liquid spray composition is shown in the following table.

| Part A | Part B |
| --- | --- |
| 5.0%-Calcium ascorbate | 0.2%-Sodium carbonate |
| 0.5%-sucralose | 0.5%-sucralose |
| 1.0%-peppermint oil | 1.0%-peppermint oil |
| 93.5%-water | 93.5%-water |

In addition to the above examples of a delivery device that delivers a pH modifier composition and/or a buffer capacity modifier composition in a convenient manner to the oral cavity, example embodiments of the present invention further include a testing device to initially test the environment characteristics within a particular patient's oral cavity. For example, the testing device can be used to determine the strength or dosage of the pH modifier and/or buffering capacity modifier in one or more of the above delivery devices such that an individualized treatment plan can be created for a particular individual. In at least one embodiment, the testing device results and the dosage of the pH and buffering capacity modifier compositions within the delivery devices can be coordinated (e.g., by number or color) such that a patient can easily know what dosage is required for the patient's particular pH levels and buffering capacity.

On example of a testing device can include a testing strip that measures both the pH and buffer capacity of saliva. For example, the testing device can include a hand-held colorimetric testing strip that can be easily covered in a patient's saliva by having the patient place the testing strip into the patient's mouth, or by placing the patient's saliva directly on the testing strip. After the patient's saliva is in contact with the testing strip, the testing strip has a corresponding color change that correlates to that individual's pH and buffering salt concentration in the patient's saliva. Thus, the testing strip can provide an easy and convenient test for a patient to accurately know the pH and buffering salt concentration within the patient's saliva.

In one example embodiment, the colorimetric testing strip can contain both the pH-testing pad and the buffering salt testing pad on the same strip, wherein the pH and buffering capacity can be measured by a single analysis. For example, the pH testing pad can be configured to measure the pH between 4.5-10, and the buffering capacity testing pad can be configured to measure the available calcium salt concentration between 0-1000 ppm.

In one example, the pH pad can be made of absorbent paper or cotton that is soaked in an aqueous pH indicator comprising various indicators such as bromocresol green, methyl red, azolitmin, bromocresol purple, bromothymol blue, phenol red, neutral red, napthophthalein, Alizarine yellow R, phenolphthalein, congo red, thymol blue, methyl orange, leucomalachite green, methyl yellow, and any like useful pH indicator. Similarly, the buffering capacity test pad can be made of absorbent paper or cotton that is soaked in a known quantity of acid or base with an aqueous alkalinity indicator(s). Thus, when the patient's saliva reacts with the known quantity of acid or base on the strip, the resulting colorimetric pH achieved correlates to a ppm buffering salt concentration. Alternatively, the calcium, phosphate, hydroxide, or carbonate ion concentration can be measured directly by color sensitive indicators that change colors with respect to the concentration of the respective anion or cation.

Both the pH testing pad and the buffering capacity testing pad can be fastened to a plastic or paper applicator test strip by an adhesive or other similar means. For example, in one embodiment the pH testing pad can be attached to a first side of the testing strip, and the buffering capacity testing pad can be attached to a second side of the testing strip. Alternatively, both the pH testing pad and the buffering capacity testing pad can be attached to the same side of the testing strip.

The completed colorimetric testing strip can then either be inserted into the mouth, or saliva can be collected into a container, in order to coat the testing pads with the patient's saliva. The patient's saliva interacts with both the pH testing strip and the buffering capacity testing strip to change colors as described above. The patient can then compare the color on the testing strip to a pre-determined colorimetric chart that corresponds to the change in pH and buffering capacities. Upon analyzing the results of the test, a patient can determine their risk level with respect to tooth decay and determine a corresponding treatment or dosage of pH modifier compositions and buffering capacity modifier compositions described above. For example, the test strip can determine the risk of cavities such that the strength and the frequency for the need of the pH modifier and/or buffering capacity modifier device or confection.

More particularly, the patients who score low in both pH and buffering capacity are placed into a high risk category of treatment wherein they receive devices or confections that sufficiently modify the pH and buffering capacity with respect to their low scores. The patients who have a moderate pH and buffering capacity are placed into a medium risk category where they receive devices and confections that modify their pH and buffering capacity customized to the level of modification that is necessary for them. The patients who have a high natural pH and buffering capacity may not even require treatment because their respective pH and buffering capacity are high enough that they do not drop below a pH level of about 6.2 even after eating a meal.

For example, a patient who has measured their pH and buffering capacity and has found that they are in the high risk category of tooth decay may be prescribed to chew two or three pieces of chewing gum for an increased concentration of pH and buffering capacity after every meal, whereas someone in the medium risk group may be required to chew only one piece of any desired confection. Alternatively the strength of the confection can be varied as to create a maximum strength and/or a regular strength composition, so a specific gum can be prescribed depending upon to which risk group the patient pertains.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental treatment system for directly controlling the pH environment within a patient's oral cavity, comprising:
   a testing device, comprising:
      a testing strip;
      a pH testing pad attached to the testing strip and configured to test the pH level of a patient's saliva; and
      a buffering capacity testing pad attached to the testing strip and configured to test the buffering capacity of a patient's saliva; and
   a delivery device, comprising:
      an oral pH modifier composition; and
      an oral buffering capacity modifier composition, wherein the testing device is used to determine the dosage of the delivery device such that the patient can customize the use of the delivery device to control the pH within the patient's oral cavity.

2. The dental treatment system recited in claim 1, wherein the delivery device is in the form of a confection.

3. The dental treatment system recited in claim 2, wherein the buffering capacity modifier composition comprises calcium ascorbate.

4. The dental treatment system recited in claim 3, wherein the calcium ascorbate has a weight percentage within the range of about 1% to about 10% of the overall weight of the confection.

5. The dental treatment system recited in claim 1, wherein the test strip comprises a first side and a second side, and wherein the pH testing pad is attached to the first side and the buffering capacity testing pad is attached to the second side.

6. The dental treatment system recited in claim 1, wherein the pH testing pad comprises an absorbent material soaked in a plurality of pH indicator compounds.

7. The dental treatment system recited in claim 1, wherein the buffering capacity testing pad comprises an absorbent material soaked in a known quantity of acid or base.

8. An oral saliva testing device, comprising:
   a test strip; and
   an oral buffering capacity test pad attached to the test strip,
   wherein the oral buffering capacity test pad measures a buffering capacity of a patient's saliva when brought into contact with the patient's saliva; and
   an oral pH test pad attached to the test strip.

9. The oral saliva testing device recited in claim 8, wherein the pH testing pad comprises an absorbent material soaked in a plurality of pH indicator compounds.

10. The oral saliva testing device recited in claim 9, wherein the buffering capacity testing pad comprises an absorbent material soaked in a known quantity of acid or base.

* * * * *